US00PP30248P3

(12) United States Plant Patent
Suphachadiwong

(10) Patent No.: US PP30,248 P3
(45) Date of Patent: Feb. 26, 2019

(54) *VANDA* PLANT NAMED 'SPCDW1517'

(50) Latin Name: ***Vanda* Jones ex R. Br.**
Varietal Denomination: SPCDW1517

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 78 days.

(21) Appl. No.: 15/530,043

(22) Filed: Nov. 23, 2016

(65) Prior Publication Data

US 2017/0156250 P1 Jun. 1, 2017

(30) Foreign Application Priority Data

Nov. 27, 2015 (QZ) ..... PBR 2015/2867

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Keith O. Robinson
(74) *Attorney, Agent, or Firm* — Samuel R. McCoy, Jr.

(57) ABSTRACT

A new and distinct *Vanda* cultivar named 'SPCDW1517' which is characterized by a branched main stem, sepals and petals which are nearly pure white at anthesis, a white labellum that is lightly suffused with red-purple, as well as the stability of these characteristics from generation to generation.

4 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1517'.

CROSS REFERENCE TO RELATED APPLICATIONS

This application claims priority to the Community Plant Variety Rights application number 2015/2867, filed Nov. 27, 2015, which is herein incorporated by reference.

BACKGROUND OF THE INVENTION

Parentage: The *Vanda* variety 'SPCDW1517' originated as a naturally occurring, whole-plant mutation of *Vanda* 'SPCDW0902' (U.S. Pat. No. 23,343), a variety developed and owned by the inventor. The inventor of 'SPCDW1517' is a commercial producer of *Vanda* and regularly discovers mutations at his greenhouse operation in Bangphra, Thailand. The variety now called 'SPCDW1517' was initially discovered in August of 2009 as one such mutation of 'SPCDW00902'.

Asexual Reproduction: Asexual reproduction of the new cultivar 'SPCDW1517', by way of mericloning, was first initiated in April of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1517' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1517'. These characteristics in combination distinguish 'SPCDW1517' as a new and distinct *Vanda* cultivar:

1. *Vanda* 'SPCDW1517' exhibits a branched main stem; and
2. *Vanda* 'SPCDW1517' exhibits petals and sepals that are nearly pure white at anthesis; and
3. *Vanda* 'SPCDW1517' exhibits a white labellum, lightly suffused with red-purple.

BOTANICAL DESCRIPTION OF THE PLANT

Figure 1:
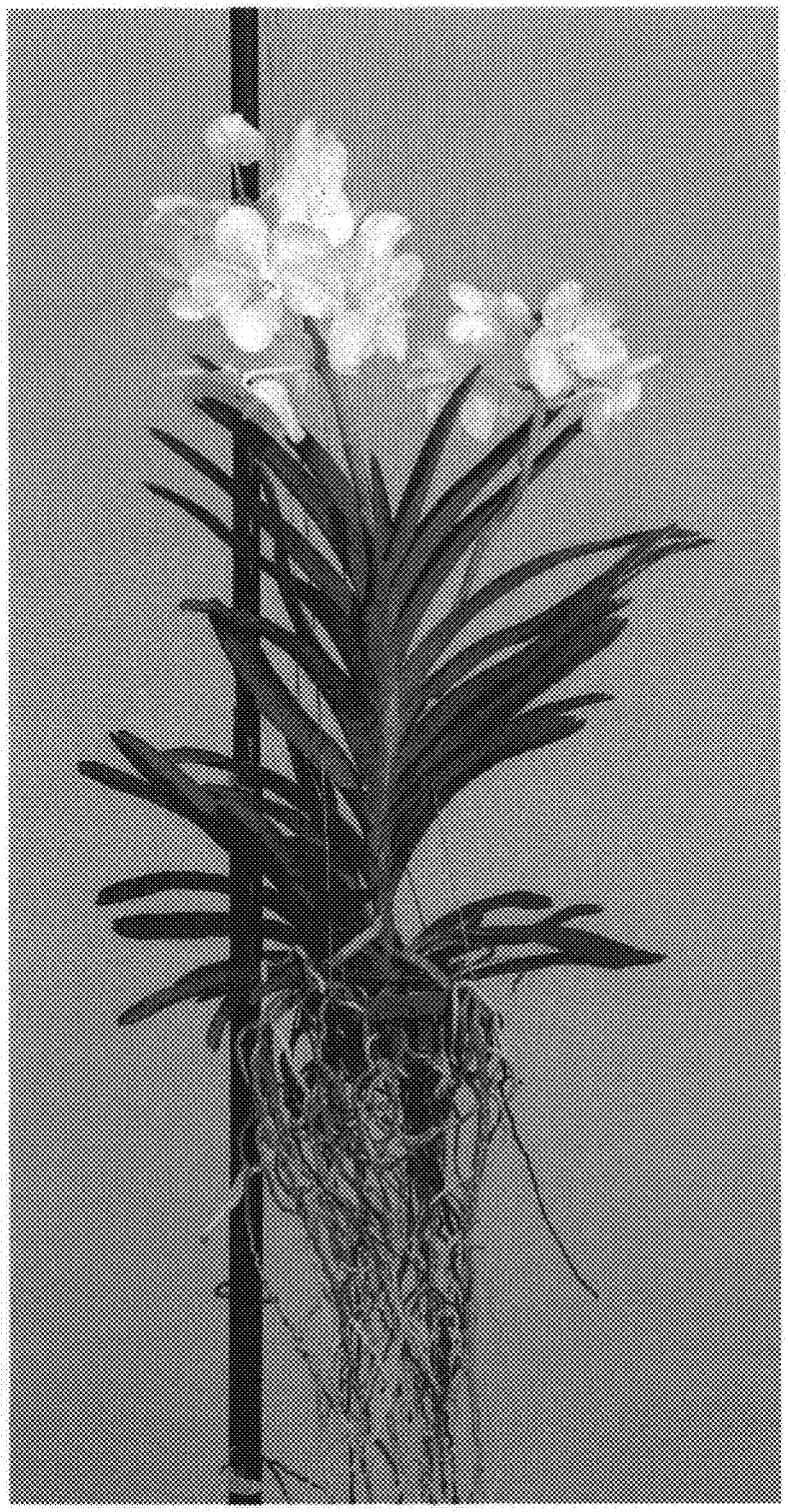
FIG. 1 illustrates, as nearly true as it is reasonably possible to make the same in color photographs of this type, an exemplary plant of 'SPCDW1517' grown in a commercial greenhouse in Honselersdijk, the Netherlands. This plant is approximately 6 years old from the time of mericloning, shown planted in an 8 by 8 cm container.
Figure 2:
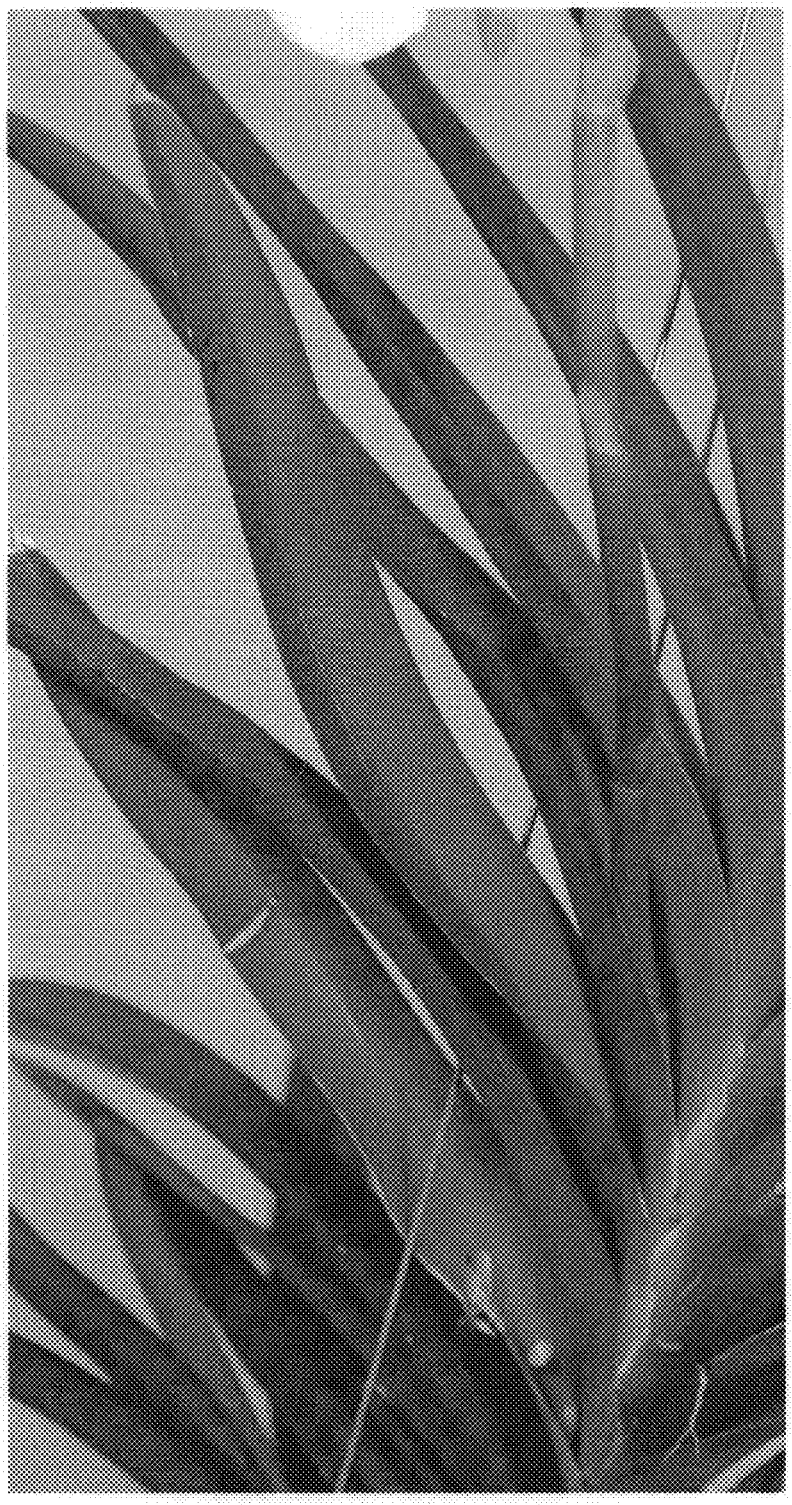
FIG. 2 illustrates, as nearly true as it is reasonably possible to make the same in color photographs of this type, the typical foliage of 'SPCDW1517'.
Figure 3:
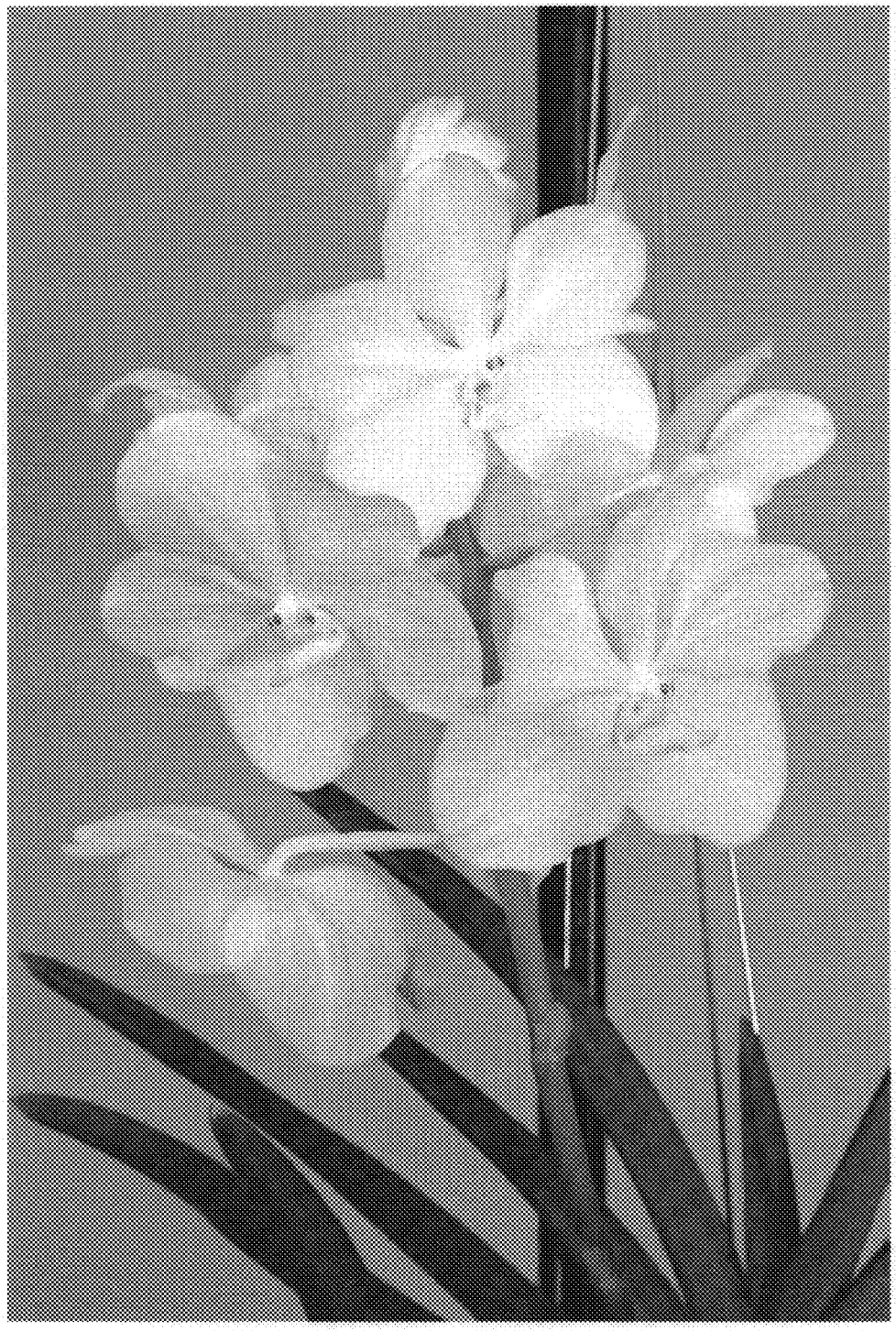
FIG. 3 illustrates, as nearly true as it is reasonably possible to make the same in color photographs of this type, the typical inflorescence of 'SPCDW1517'.
Figure 4:
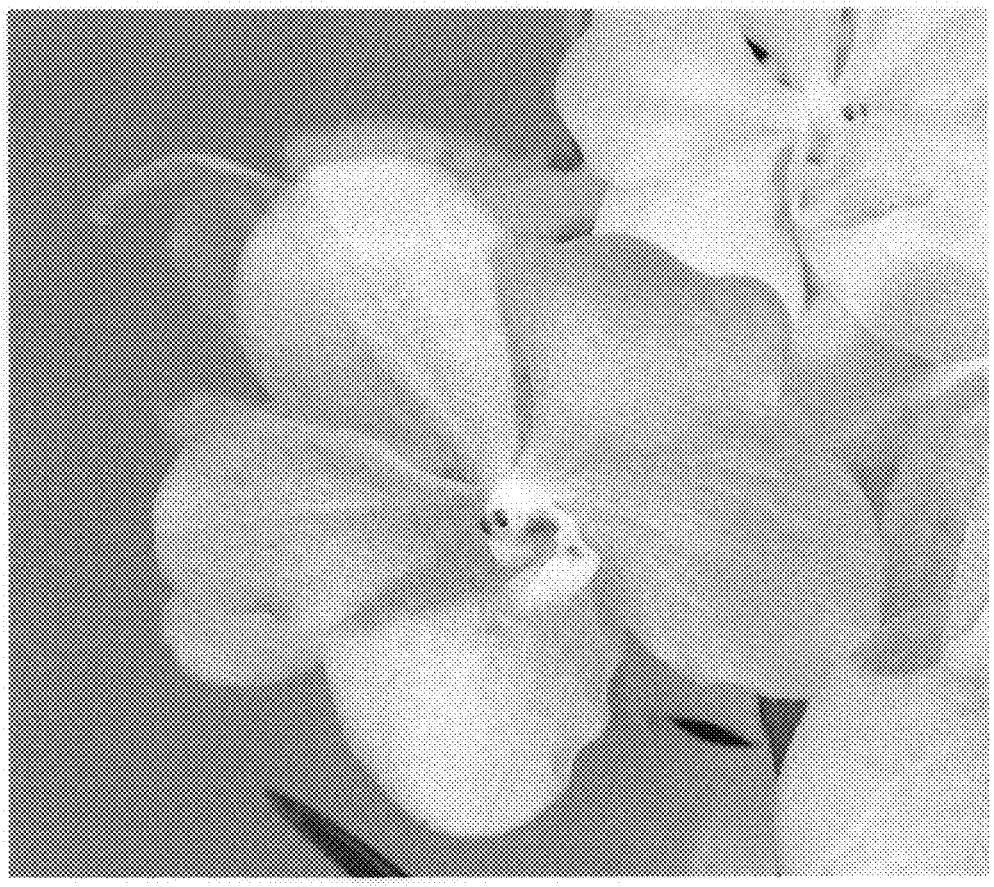
FIG. 4 illustrates, as nearly true as it is reasonably possible to make the same in color photographs of this type, the typical flower of 'SPCDW1517'.

The following observations and measurements made in October of 2016 describe averages from a sample set of six specimens of six year-old 'SPCDW1517' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1517' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1517' and comparisons with other varieties of *Vanda* are provided below.

Plant description:

*Growth habit*.—Perennial; monopodial, upright. Single monopodial leafy stem, with an average of one lateral branch growing from the base of the main stem; flowers carried slightly above the leaf plane with inflorescences growing from the leaf axils.

*Average height from base (plant grown in hanging basket, so no soil line present) to foliar plane*.—41.9 cm.

*Average height from base (plant grown in hanging basket, so no soil line present) to top of floral plane*.—51.5 cm.

*Plant spread*.—Average of 37.0 cm.

*Appropriate container size*.—8 cm by 8 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately to densely rooting; with aerial roots only.

*Dimensions, mature roots*.—63.8 cm long with a diameter of 0.5 cm, on average.

*Texture*.—Very fleshy; non-fibrous.

*Color*.—Greyed-green, nearest to RHS 192B; root apex is yellow-green, nearest to RHS 144A.

Stem:

*Branching habit*.—Monopodial, with an average of one lateral branch growing from the base of the main stem.

*Number of primary (main) stems per plant*.—One.

*Number of secondary (lateral) branches per plant*.—One.

*Main stem*.—Appearance and shape — Circular, formed by the leaf sheaths. Length — 26.2 cm. Diameter — 0.9 cm. Internode length — 0.6 cm. Luster — Matte. Aspect, main stem — Near vertical. Strength — Very strong. Color, juvenile — Yellow-green, nearest to RHS 145C. Color, mature — Yellow-green, nearest to RHS 145C. Color at internodes — Yellow-green, nearest to RHS 145C. Pubescence — Glabrous.

*Lateral branch*.—Appearance and shape — Circular, formed by the leaf sheaths. Length — Approximately 8.7 cm. Diameter — 0.9 cm. Internode length — 0.6 cm. Luster — Matte. Aspect, main stem — At an approximate angle of 50 degrees to the main stem. Strength — Very strong. Color, juvenile — Yellow-green, nearest to RHS 145C. Color, mature — Yellow-green, nearest to RHS 145C. Color at internodes — Yellow-green, nearest to RHS 145C. Pubescence — Glabrous.

Foliage:

*Arrangement*.—Distichous.

*Dimensions*.—21.1 cm long, excluding the sheath, and 2.5 cm wide.

*Shape of blade*.—Ligulate; moderately carinate.

*Aspect*.—Slightly curved.

*Apex*.—Unequal praemorse.

*Base*.—Sheathing.

*Sheath dimensions*.—3.4 cm long and 1.2 cm wide, on average.

*Sheath color*.—Yellow-green, a mixture of RHS 145A and 151C.

*Margin*.—Entire.

*Pubescence, texture and luster of adaxial surface*.—Glabrous, smooth, and matte.

*Pubescence, texture and luster of abaxial surface*.—Glabrous, smooth, and very slightly glossy.

*Color*.—Variegation — Absent. Juvenile foliage, adaxial surface — Green, in between RHS 143A and 143B. Juvenile foliage, abaxial surface — Green, nearest to RHS 143A. Mature foliage, adaxial surface — Green, nearest to RHS 137B. Mature foliage, abaxial surface — Yellow-green, nearest to RHS 146B.

*Venation*.—Parallel.

*Venation color, adaxial surface*.—Green, nearest to RHS 137B.

*Venation color, abaxial surface*.—Yellow-green, RHS N144C.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Quantity of inflorescence per plant*.—One.

*Flowers per inflorescence*.—Average of 10.

*Flowers per plant*.—18 open flowers and 2 flower buds.

*Inflorescence height*.—Approximately 14.7 cm (measured from base of lowest flower to top of upper flower).

*Inflorescence diameter*.—Approximately 15.3 cm.

*Peduncle*.—Dimensions — Approximately 29.1 cm long and 0.6 cm wide. Aspect — Generally at a 35 degree angle to lateral branch axis. Strength — Moderately strong. Texture and luster — Glabrous and moderately glossy. Color — Yellow-green, nearest to RHS 144C.

Bud:

*Length*.—Average of 2.0 cm.

*Diameter*.—Average horizontal diameter is 1.4 cm; the vertical diameter is 1.7 cm.

*Shape*.—Cubic, with a deltoid apex which is pointed downward.

*Pubescence, texture and luster*.—Glabrous, smooth and very slightly glossy.

*Color*.—Yellow-green, nearest to RHS 150D.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals touching the dorsal sepal and slightly overlapping the lateral sepals; sepals do not overlap one another.

*Aspect*.—Flowers are outward-facing to slightly nodding.

*Vertical height*.—Approximately 8.2 cm.

*Diameter*.—Approximately 7.8 cm.

*Depth*.—Approximately 2.7 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.3 cm. Width — Approximately 3.3 cm. Shape — Broad ovate. Apex — Undeeply retuse to obtuse. Base — Cuneate. Margin — Entire; not undulated to very slightly undulated. Pubescence, texture and luster of upper surface — Glabrous, velvety and matte. Pubescence, texture and luster of lower surface — Glabrous, velvety and matte. Color when opening, upper surface — White, nearest to RHS NN155B, and very lightly suffused with green-white, nearest to RHS 157D. Color when opening, lower surface — White, nearest to RHS NN155B, and very lightly suffused with green-white, nearest to RHS 157D. Color when fully opened, upper surface — White, nearest to NN155D. Color when fully opened, lower surface — White, nearest to NN155D. Fading, upper surface — Not fading. Fading, lower surface — Not fading. Venation — Densely reticulate. Venation color, fully opened, upper surface — White, nearest to NN155D. Venation color, fully opened, lower surface — White, nearest to NN155D.

*Labellum*.—Shape — Three-lobed; the shape of the lateral lobes is triangular, and the aspect is involute; the shape of the central lobe is narrow triangular, and the aspect is revolute. Length — Central lobe — Approximately 1.8 cm. Lateral lobes — Approximately 0.6 cm. Width — Central lobe — Approximately 1.0 cm. Lateral lobes — Approximately 0.5 cm. Apex — Central lobe — Strongly emarginate. Lateral lobes — Emarginate. Base — Central lobe — Cuneate. Lateral lobes — Cuneate. Margin — Central lobe — Entire; not undulate. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Green-white, nearest to RHS 157A, and suffused with yellow at the base, nearest to RHS 13C. Lateral lobes — White, nearest to RHS NN155A, and suffused with green-white, nearest to RHS 157D; dotted red-purple, nearest to RHS N74D, and yellow-orange, in between RHS 17B and 17C, at the base. Color when opening, lower surface — Central lobe — Yellow-green, nearest to RHS 145D, and fading to white towards the base, nearest to RHS 155B. Lateral lobes — White, nearest to RHS NN155B. Color when fully opened, upper surface — Central lobe — White, nearest to RHS NN155A, and very lightly suffused with red-purple at the apex, nearest to RHS 69D. Lateral lobes — White, nearest to RHS NN155B; dotted red-purple, nearest to RHS N74D. Color when fully opened, lower surface — Central lobe — White, nearest to RHS NN155D, and lightly suffused with green-white, nearest to RHS 157D; very lightly suffused with red-purple at the apex, nearest to RHS 69D. Lateral lobes — White, nearest to RHS NN155D. Fading, upper surface — Not fading. Fading, lower surface — Not fading. Venation — Densely reticulate. Venation color, fully opened, upper surface — Central lobe — White, nearest to NN155A, and very lightly suffused with red-purple at the apex, nearest to RHS 69D. Lateral lobes — White, nearest to RHS NN155B; dotted red-purple, nearest to RHS N74D. Venation color, fully opened, lower surface — Central lobe — White, nearest to RHS NN155D, and lightly suffused with green-white, nearest to RHS 157D; very lightly suffused with red-purple at the apex, nearest to RHS 69D. Lateral lobes — White, nearest to RHS NN155D.

*Callosities*.—Dimensions — 1.2 cm long and 0.6 cm wide, on average. Color — White, nearest to RHS NN155A.

*Spurs*.—Quantity — Average of 1. Length — Approximately 0.7 cm. Diameter — Approximately 0.2 cm. Vertical height — Approximately 0.4 cm, at the base. Shape — Short triangular. Apex — Bluntly acute. Base — Broad cuneate. Pubescence, texture and luster — Glabrous, smooth, and slightly glossy. Color — White, nearest to RHS N155D, and very slightly suffused with red-purple, nearest to RHS 69D.

*Sepals*.—Quantity — Average of 3 unfused sepals. Arrangement — One dorsal sepal and two lateral sepals. Length — Dorsal sepal — Approximately 4.4 cm. Lateral sepals — Approximately 4.6 cm. Width — Dorsal sepal — Approximately 3.3 cm. Lateral sepals — Approximately 3.7 cm. Shape — Dorsal sepal — Broad ovate. Lateral sepals — Broad ovate. Apex — Dorsal sepal — Obtuse. Lateral sepals — Obtuse. Base — Dorsal sepal — Cuneate. Lateral sepals — Cuneate. Margin — Dorsal sepal — Entire; slightly undulated. Lateral sepals —

Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to RHS NN155B, and suffused with yellow-green towards the apex, a mixture of RHS 145D and RHS 150D. Lateral sepals — White, nearest to RHS NN155B, and suffused with yellow-green towards the apex, a mixture of RHS 145D and RHS 150D. Color when opening, lower surface — Dorsal sepal — White, nearest to RHS NN155B, and suffused with yellow-green towards the apex, a mixture of RHS 145D and RHS 150D. Lateral sepals — White, nearest to RHS NN155B, and suffused with yellow-green towards the apex, a mixture of RHS 145D and RHS 150D. Color when fully opened, upper surface — Dorsal sepal — White, nearest to RHS NN155D but whiter; no corresponding R.H.S. color chart designation. Lateral sepals — White, nearest to RHS NN155D but whiter; no corresponding R.H.S. color chart designation. Color when fully opened, lower surface — Dorsal sepal — White, nearest to RHS NN155D but whiter; no corresponding R.H.S. color chart designation. Lateral sepals — White, nearest to RHS NN155D but whiter; no corresponding R.H.S. color chart designation. Fading, upper surface — Not fading. Fading, lower surface — Not fading. Venation — Densely reticulate. Venation color, fully opened, upper surface — Dorsal sepal — White, nearest to RHS NN155D but whiter; no corresponding R.H.S .color chart designation. Lateral sepals — White, nearest to RHS NN155D but whiter; no corresponding R.H.S. color chart designation. Venation color, fully opened, lower surface — Dorsal sepal — White, nearest to RHS NN155D but whiter; no corresponding R.H.S. color chart designation. Lateral sepals — White, nearest to RHS NN155D but whiter; no corresponding R.H.S. color chart designation.

*Pedicels*.—Length — Approximately 4.4 cm. Diameter — Approximately 0.3 cm. Angle — Approximately 70 degree angle to peduncle axis. Strength — Moderate. Texture — Glabrous, axially angled with 5 "ribs", axially twisted (due to resupination). Luster — Glossy. Color — A mixture of white, nearest to RHS NN155B, and green-white, nearest to RHS 157D, and suffused with yellow-green, nearest to RHS 145D, towards the proximal end.

*Bract*.—Quantity — One bract present at the base of each pedicel. Shape — Broad ovate; folded around the base of each pedicel. Dimensions — Average of 1.1 cm long and 1.0 cm wide. Apex — Broad acute. Base — Broad cuneate. Margins — Entire. Color, both surfaces — Yellow-green, nearest to RHS 154B.

Reproductive organs:

*Column*.—Length — Approximately 0.6 cm. Diameter — Approximately 0.5 cm. Color — White, RHS NN155A.

*Ovary*.—Position — Inferior. Diameter — Approximately 0.2 cm. Color — Yellow-green, RHS 150C.

*Pollinia color*.—Yellow-orange, RHS 15A.

Seed and fruit: No fruit and seed production has been detected to date.

COMPARISON WITH THE PARENT PLANT AND MOST SIMILAR *VANDA* CULTIVAR KNOWN TO THE INVENTOR

Plants of the new cultivar 'SPCDW1517' differ from the *Vanda* parent plant 'SPCDW0902' (U.S. Pat. No. 23,343) by the characteristics described in Table 1.

TABLE 1

| Characteristic | 'SPCDW1517' | 'SPCDW0902' |
|---|---|---|
| Flower size. | Larger than 'SPCDW0902'. | Smaller than 'SPCDW1512'. |
| General coloration of petals when fully opened. | Nearly white. | Relatively less white and suffused with yellow-green. |
| General coloration of sepals when fully opened. | Very white. | Relatively less white and suffused with yellow-green. |
| Overlapping of petals and sepals. | Less overlapped when compared to 'SPCDW0902'. | More overlapped when compared to 'SPCDW1517'. |
| Apex of dorsal sepal. | Less rounded than 'SPCDW0902'. | More rounded than 'SPCDW1517'. |
| General coloration of the central lobe of the labellum when fully opened. | Nearly white; very lightly suffused with red-purple. | Yellow-green. |
| General coloration of lateral lobes of the labellum when fully opened. | Nearly white. | Relatively less white and suffused with yellow-green. |
| Leaf width. | Broader. | Narrower. |

COMPARISON WITH THE MOST SIMILAR *VANDA* CULTIVAR KNOWN TO THE INVENTOR

Plants of the new cultivar 'SPCDW1517' are most similar to the cultivar, *Vanda* 'SPCDW1602' (U.S. Plant patent application Ser. No. 15/731,661). A comparison of 'SPCDW1517' with *Vanda* 'SPCDW1602' is described in Table 2.

TABLE 2

| Characteristic | 'SPCDW1517' | 'SPCDW1602' |
|---|---|---|
| Flower size. | Smaller than 'SPCDW1602'. | Larger than 'SPCDW1517'. |
| General coloration of the petals when fully opened. | Nearly white. | Light pink with dark purple reticulate venation. |
| Color pattern on the petals and sepals. | None. | Netted. |
| General coloration of the central lobe of the labellum. | Nearly white; very lightly suffused with red-purple. | Lighter pink. |
| General coloration of the column. | White. | Lighter pink. |

That which is claimed is:

1. A new and distinct variety of *Vanda* plant named 'SPCDW1517', substantially as described and illustrated herein.

* * * * *